(12) United States Patent
Schiemann et al.

(10) Patent No.: US 9,765,366 B2
(45) Date of Patent: Sep. 19, 2017

(54) BIOTECHNOLOGICAL METHOD FOR PRODUCING BUTANOL AND BUTYRIC ACID

(71) Applicants: Wilhelm Krispin, Mering (DE); Monika Johanna Krispin, Mering (DE)

(72) Inventors: Yvonne Schiemann, Essen (DE); Liv Reinecke, Essen (DE); Thomas Haas, Muenster (DE); Dirk Weuster-Botz, Munich (DE); Harald Krispin

(73) Assignee: Evonik Degussa GmbH, Essen (DE)

( * ) Notice: Subject to any disclaimer, the term of this patent is extended or adjusted under 35 U.S.C. 154(b) by 9 days.

(21) Appl. No.: 14/380,483

(22) PCT Filed: Feb. 22, 2013

(86) PCT No.: PCT/EP2013/053523
§ 371 (c)(1),
(2) Date: Aug. 22, 2014

(87) PCT Pub. No.: WO2013/124401
PCT Pub. Date: Aug. 29, 2013

(65) Prior Publication Data
US 2015/0284747 A1    Oct. 8, 2015

(30) Foreign Application Priority Data

Feb. 22, 2012    (EP) .................................. 12156493

(51) Int. Cl.
C12N 1/00    (2006.01)
C12P 7/52    (2006.01)
C12P 7/16    (2006.01)

(52) U.S. Cl.
CPC .................. *C12P 7/52* (2013.01); *C12P 7/16* (2013.01); *Y02E 50/10* (2013.01)

(58) Field of Classification Search
None
See application file for complete search history.

(56) References Cited

U.S. PATENT DOCUMENTS

| 4,560,658 | A | * | 12/1985 | Datta | ....................... | C12N 1/38 |
| | | | | | | 435/160 |
| 5,192,673 | A | * | 3/1993 | Jain | ....................... | C12R 1/145 |
| | | | | | | 435/160 |
| 6,620,970 | B2 | | 9/2003 | Schiffer et al. | | |
| 6,639,108 | B2 | | 10/2003 | Schiffer et al. | | |
| 6,861,540 | B2 | | 3/2005 | Herwig et al. | | |
| 6,878,836 | B2 | | 4/2005 | Haas et al. | | |
| 7,030,052 | B2 | | 4/2006 | Stochniol et al. | | |
| 7,049,450 | B2 | | 5/2006 | Hofen et al. | | |
| 7,091,384 | B2 | | 8/2006 | Jaeger et al. | | |
| 7,157,610 | B2 | | 1/2007 | Hofen et al. | | |
| 7,507,862 | B2 | | 3/2009 | Stochniol et al. | | |
| 7,754,778 | B2 | | 7/2010 | Knott et al. | | |
| 7,879,938 | B2 | | 2/2011 | Hager et al. | | |
| 7,923,225 | B2 | | 4/2011 | Mueller et al. | | |
| 8,216,813 | B2 | | 7/2012 | Thum et al. | | |
| 8,293,509 | B2 | * | 10/2012 | Simpson | .................. | C12P 7/065 |
| | | | | | | 435/132 |
| 8,349,596 | B2 | | 1/2013 | Mueller et al. | | |
| 8,349,907 | B2 | | 1/2013 | Henning et al. | | |
| 8,372,595 | B2 | | 2/2013 | Schaffer et al. | | |
| 8,378,127 | B2 | | 2/2013 | Dingerdissen et al. | | |
| 8,399,658 | B2 | | 3/2013 | Hengstermann et al. | | |
| 8,404,470 | B2 | | 3/2013 | Thum et al. | | |
| 8,445,720 | B2 | | 5/2013 | Hannen et al. | | |
| 8,486,677 | B2 | | 7/2013 | Thum et al. | | |
| 8,604,227 | B2 | | 12/2013 | Petrat et al. | | |
| 8,703,451 | B2 | | 4/2014 | Haas et al. | | |
| 8,703,993 | B2 | | 4/2014 | Hannen et al. | | |
| 8,796,000 | B2 | | 8/2014 | Thum et al. | | |
| 8,809,576 | B2 | | 8/2014 | Schraven et al. | | |
| 9,000,223 | B2 | | 4/2015 | Micoine et al. | | |
| 9,034,618 | B2 | * | 5/2015 | Adams | ..................... | C12N 1/20 |
| | | | | | | 435/160 |
| 2002/0087036 | A1 | | 7/2002 | Haas et al. | | |
| 2003/0212298 | A1 | | 11/2003 | Brasse et al. | | |
| 2010/0068773 | A1 | | 3/2010 | Marx et al. | | |

(Continued)

FOREIGN PATENT DOCUMENTS

CN         101952393 A    1/2011
WO    WO 2008/148640 A1    12/2008

(Continued)

OTHER PUBLICATIONS

Bruant et al. "Genomic analysis of carbon monoxide utilization and butanol production by Clostridium carboxidivorans strain P7". PLoS ONE, Sep. 2010, vol. 5, issue 9, e13033, pp. 1-12.*
Kim et al. Applied and Environmental Microbiology, Oct. 1984, vol. 48, No. 4, pp. 764-770.*
Chen, C.-K., et al., "Acetate enhances solvent production and prevents degeneration in Clostridium beijerinckii BA101", Applied Microbiology Biotechnology, vol. 52, pp. 170-173, (1999) XP 002678047.
Jang, Y.-S., et al., "Butanol production from renewable biomass: Rediscovery of metabolic pathways and metabolic engineering", BIOTECHNOLOGY JOURNAL, vol. 7, pp. 186-198, (Feb. 2012) XP 002678028.
Smchmidt, M., et al., "Reaction engineering studies of acetone-butanol-ethanol fermentation with Clostridium acetobutylicum", Biotechnology Journal, vol. 7, pp. 656-661, (Dec. 28, 2012) XP 002678029.

(Continued)

*Primary Examiner* — Vera Afremova
(74) *Attorney, Agent, or Firm* — Oblon, McClelland, Maier & Neustadt, L.L.P.

(57)    ABSTRACT

The present invention relates to a method for producing C4 bodies, preferably butyric acid and/or butanol, comprising the steps contacting an aqueous medium comprising an acetogenic bacterial cell in an aqueous medium with syngas and incubating the mixture obtained in step a) at a temperature between 0 and 100° C. for at least 30 minutes, wherein the aqueous medium comprises, in step b), ethanol and/or acetate at a total combined concentration is at least $0.1\ gL^{-1}$.

20 Claims, 4 Drawing Sheets

(56) References Cited

U.S. PATENT DOCUMENTS

| | | |
|---|---|---|
| 2010/0167360 A1 | 7/2010 | Thum et al. |
| 2010/0190224 A1 | 7/2010 | Pötter et al. |
| 2010/0248325 A1 | 9/2010 | Eckstein et al. |
| 2010/0261237 A1 | 10/2010 | Verseck et al. |
| 2010/0266518 A1 | 10/2010 | Springer et al. |
| 2010/0291644 A1 | 11/2010 | Marx et al. |
| 2010/0324257 A1 | 12/2010 | Karau et al. |
| 2011/0039313 A1 | 2/2011 | Verseck et al. |
| 2011/0118433 A1 | 5/2011 | Pötter et al. |
| 2011/0118504 A1 | 5/2011 | Haas et al. |
| 2011/0171702 A1 | 7/2011 | Reinecke et al. |
| 2011/0251399 A1 | 10/2011 | Dingerdissen et al. |
| 2012/0034665 A1 | 2/2012 | Haas et al. |
| 2012/0041216 A1 | 2/2012 | Sieber et al. |
| 2012/0071577 A1 | 3/2012 | Pfeffer et al. |
| 2012/0077932 A1 | 3/2012 | Pfeffer et al. |
| 2012/0264182 A1 | 10/2012 | Reinecke et al. |
| 2012/0315366 A1 | 12/2012 | Zehnacker et al. |
| 2013/0035403 A1 | 2/2013 | Schaffer et al. |
| 2013/0052700 A1 | 2/2013 | Pötter et al. |
| 2013/0092233 A1 | 4/2013 | Pawlik et al. |
| 2013/0130319 A1 | 5/2013 | Schaffer et al. |
| 2013/0164797 A1 | 6/2013 | Gielen et al. |
| 2013/0165672 A1 | 6/2013 | Klasovsky et al. |
| 2013/0165685 A1 | 6/2013 | Hannen et al. |
| 2013/0183725 A1 | 7/2013 | Pötter et al. |
| 2013/0245276 A1 | 9/2013 | Klasovsky et al. |
| 2013/0299750 A1 | 11/2013 | Hermasch et al. |
| 2013/0331580 A1 | 12/2013 | Klasovsky et al. |
| 2014/0039210 A1 | 2/2014 | Erhardt et al. |
| 2014/0039223 A1 | 2/2014 | Klasovsky et al. |
| 2014/0054224 A1 | 2/2014 | Erhardt et al. |
| 2014/0120587 A1 | 5/2014 | Haas et al. |
| 2014/0141478 A1 | 5/2014 | Schaffer et al. |
| 2014/0178948 A1 | 6/2014 | Schaffer et al. |
| 2014/0186905 A1 | 7/2014 | Schaffer et al. |
| 2014/0199736 A1 | 7/2014 | Köhler et al. |

FOREIGN PATENT DOCUMENTS

| | | |
|---|---|---|
| WO | 2009/105372 A1 | 8/2009 |
| WO | WO 2011/154503 A1 | 12/2011 |
| WO | WO 2013/024111 A1 | 2/2013 |
| WO | WO 2013/024114 A2 | 2/2013 |
| WO | WO 2013/083374 A1 | 6/2013 |
| WO | WO 2013/083412 A1 | 6/2013 |
| WO | WO 2013/092426 A1 | 6/2013 |
| WO | WO 2013/124401 A1 | 8/2013 |
| WO | WO 2013/167663 A2 | 11/2013 |
| WO | WO 2013/186340 A1 | 12/2013 |

OTHER PUBLICATIONS

Tirado-Acevedo, O., et al., "Influence of Carbon Source Pre-Adaptation on Clostridium Ijungdahlii Growth and Product Formation", Bioprocessing Biotechinque, pp. 1-5, (2011) XP 0055036788.

Perez, J., et al., "Biocatalytic Reduction of Short-Chain Carboxylic Acids Into Their Corresponding Alcohols With Syngas Fermentation", Biotechnology and Bioengineering, vol. 110, No. 4, pp. 1066-1077, (Apr. 2013) XP 002694318.

International Search Report Issued Apr. 8, 2013 in PCT/EP13/053523 Filed Feb. 22, 2013.

* cited by examiner

BIOTECHNOLOGICAL METHOD FOR PRODUCING BUTANOL AND BUTYRIC ACID

The present invention relates to a method for producing C4 bodies, preferably butyric acid and/or butanol, comprising the steps contacting an acetogenic bacterial cell in an aqueous medium with syngas and incubating the mixture obtained in step a) at a temperature between 0 and 100° C. for at least 30 minutes, wherein the aqueous medium comprises, in step b), ethanol and/or acetate at a total combined concentration of at least 0.1 g $L^{-1}$.

The era of non-renewable fossil fuels is coming to an end. While chemists have been able to rely on a virtually unlimited supply of coal, petroleum and natural gas until now, the availability of such resources, formed by bacteria, plankton, plant and animal matter buried in ocean sediments over millions of years, is bound to be limiting in the very near future. Moreover, burning fossil fuels has been linked with the increase in atmospheric concentrations of $CO_2$ and associated climate changes, most notably global warming. Therefore, next generation processes for the production of bulk chemicals such as butanol, butyric acid and derivates thereof, conventionally derived from fossil resources, will have to start with renewable resources, i. e. materials that are easily and, in terms of geological time scales, rapidly replenishable.

Industrial biotechnology, i. e. the application of biocatalysts such as enzymes or catalyticall competent organisms as industrial catalysts, offers alternatives to many conventional processes using fossil resources as input. Not only are biocatalysts able to convert compounds made from renewable materials, often agricultural or process wastes that would otherwise have to be disposed of, but they do not require the use of toxic compounds and, last but not least, reduce greenhouse gas emissions compared to conventional approaches.

Numerous methods for producing butanol ($CH_3$—$CH_2$—$CH_2$—$CH_2$—OH) and butyric acid ($CH_3$—$CH_2$—$CH_2$—COOH, also referred to as butyrate) and C4 derivatives thereof have been reported in the prior art, but most of them rely on cracking fossil fuels and oxidising the resulting short hydrocarbons. By contrast, few processes have been described that start with carbon in the form of carbon monoxide or carbon dioxide, compounds available from exhaust gases and example syngas.

Syngas, a term referring to various mixtures comprising at least one of water and hydrogen and at least one of carbon monoxide and carbon dioxide, is a renewable source of carbon and is readily available throughout the world, as processes for its production using various starting materials are known, including steam reforming of natural gas or liquid hydrocarbons and the gasification of coal or biomass.

The use of syngas for the production of compounds comprising carbon chains has been reported in the prior art. However, the processes previously described depend on the addition of additional substrates, in particular carbon hydrates such as glucose. Processes based on microbial consumption of syngas as carbon source lead to rather unsatisfactory yields of the compounds desired.

Therefore, the problem underlying the present invention is to provide a method for producing C4 bodies, preferably butanol and/or butyric acid, starting from carbon monoxide or carbon dioxide, preferably in the form of syngas.

Another problem underlying the present invention is to provide a method for producing C4 bodies, preferably butanol and/or butyric acid, starting from carbon monoxide or carbon dioxide, which method is improved compared to state-of-the-art methods in terms of yield and/or purity of butanol and/or butyric acid formed or the proportion of C4 bodies, preferably butanol and/or butyric acid, made from syngas-derived carbon atoms rather than other carbon sources present, in particular carbohydrates such as glucose.

Another problem underlying the present invention is to provide a method for producing C4 bodies starting with syngas, wherein the yield of C4 products relative to the carbon-containing reactants other than carbon monoxide and carbon dioxide is improved, i.e. the amount of carbon compounds other than carbon monoxide and carbon dioxide required for the synthesis is reduced.

In a first aspect, the problem underlying the present invention is solved by a method for producing C4 bodies, preferably butyric acid and/or butanol, comprising the steps:
  a) contacting an acetogenic bacterial cell in an aqueous medium with syngas under anaerobic conditions,
  b) incubating the mixture obtained in step a) at a temperature between 0 and 100° C. for at least 30 minutes, wherein the aqueous medium comprises, in step b), ethanol and/or acetate at a total combined concentration exceeding 0.1 g $L^{-1}$.

In a first embodiment of the first aspect of the present invention, the problem is solved by a method, wherein the ethanol and/or acetate is exogenously produced ethanol and/or acetate.

In a second embodiment of the first aspect, which is also an embodiment of the first embodiment of the first aspect, the problem is solved by a method, wherein the total combined concentration of ethanol and/or acetate is 0.5 g $L^{-1}$ to 20 g $L^{-1}$.

In a third embodiment of the first aspect, which is also an embodiment of the first to second embodiments of the first aspect, the problem is solved by a method, wherein the syngas comprises 40 to 100, preferably 40 to 95% CO.

In a fourth embodiment of the first aspect, which is also an embodiment of the first to third embodiments of the first aspect, the problem is solved by a method, wherein the syngas comprises less than 10% $CO_2$.

In a fifth embodiment of the first aspect, which is also an embodiment of the first to fourth embodiments of the first aspect, the problem is solved by a method, wherein the syngas comprises less than 10% CO.

In a sixth embodiment of the first aspect, which is also an embodiment of the first to fifth embodiments of the first aspect, the problem is solved by a method, wherein the method comprises the step
  c) separating and, optionally, recycling ethanol and/or acetate from the mixture following step b).

In a seventh embodiment of the first aspect, which is also an embodiment of the first to sixth embodiments of the first aspect, the problem is solved by a method, wherein the acetogenic bacterial cell is selected from the group comprising *Clostridium*, *Moorella* and *Carboxythermus* and is preferably *Clostridium carboxidivorans*.

In an eighth embodiment of the first aspect, which is also an embodiment of the first to seventh embodiments of the first aspect, the problem is solved by a method, wherein the pH in steps a) and b) is maintained between 3 and 7, preferably 4 to 6, more preferably 5 to 5.5.

In a ninth embodiment of the first aspect, which is also an embodiment of the first to eighth embodiments of the first aspect, the problem is solved by a method wherein step b) is carried out at a temperature between 15° C. and 45° C., preferably 30° C. to 40° C.

In a tenth embodiment of the first aspect, which is also an embodiment of the first to ninth embodiments of the first aspect, the problem is solved by a method, wherein the syngas provides more than 80, preferably more than 90% of the carbon present initially in step a).

In a eleventh embodiment of the first aspect, which is also an embodiment of the first to tenth embodiments of the first aspect, the problem is solved by a method, wherein the process is run in a continuous mode.

In a twelfth embodiment of the first aspect, which is also an embodiment of the first to eleventh embodiment of the first aspect, wherein step b) is carried out in the absence of carbohydrates.

The problem underlying the present invention is solved, in a second aspect, by a use of ethanol and/or acetate for increasing the proportion of syngas converted by an acetogenic bacterial cell to C4 bodies, preferably butyric acid and/or butanol.

In a first embodiment of the second aspect, the problem is solved by a use, wherein the ethanol and/or acetate is exogenously produced ethanol and/or acetate and is preferably added to an aqueous medium comprising the acetogenic bacterial cell prior to the accumulation of detectable quantities of ethanol and/or acetate produced endogenously by said cell.

In a second embodiment of the second aspect, which is also an embodiment of the first embodiment of the second aspect, the problem is solved by a use, wherein acetate and/or ethanol is present in an aqueous medium comprising the acetogenic bacterial cell at a total combined concentration of ethanol and/or acetate exceeding 0.5 g $L^{-1}$, but not 20 g $L^{-1}$.

In a third embodiment of the second aspect, which is also an embodiment of the first to second embodiments of the second aspect, the problem is solved by a use, wherein the acetogenic bacterial cell is selected from the group comprising *Clostridium, Moorella* and *Carboxythermus* and is preferably *Clostridium carboxidivorans*.

Without wishing to be bound by any theory, the present inventors theorise that the presence of ethanol or acetate induces expression of genes essential for the conversion of syngas to C4 bodies, preferably butanol and/or butyric acid, thus increasing an acetogenic bacterial cell's capacity to metabolise carbon monoxide and carbon dioxide from syngas.

The present invention centers around the production of C4 bodies, preferably butanol and/or butyric acid, using an acetogenic bacterial cell. In a preferred embodiment, the term "acetogenic bacterial cell", as used herein refers to a bacterial or archaeal cell that is capable of producing acetate under anaerobic conditions, preferably using hydrogen as an electron donor and carbon dioxide as an electron acceptor or carbon monoxide instead of carbon dioxide. A multitude of acetogenic bacteria have been disclosed in the prior art, including but not limited to *Clostridium aceticum* (Wieringa, K. T. (1936), J. Microbiol. Serol. 3, 263-273), *Acetobacterium woodi* (Balch, W. E., Schobert, S., Tanner, R. S., and Wolfe, R. S. (1977), Int. J. Sys. Bacteriol. 27, 335-361), *Clostridium thermaceticum* (Fontaine, F. E, Peterson, W. H., McCoy, E. and Johnson, M. J. (1942), J. Bact. 43, 701-715), *Clostridium lungdahlii* (WO0068407), *Clostridium autoethanogenum* (Aribini et al., Archives of Microbiology 161, 345-351), *Moorella* sp. HUC22-1 (Sakai et al., Biotechnology Letters 29, 1697-1612) and those of the genus *Carboxydothermus* (Svetlichny et al. (1991), Systematic and Applied Microbiology 14, 254-260). These and other acetogenic bacterial cells are commercially available, for example from the American Tissue and Culture Collection (ATTC), USA, or from the Deutsche Sammlung von Mikroorganismen and Zellkulturen GmbH, Braunschweig, Germany. Within the scope of the present invention is also a mixed culture comprising at least two acetogenic bacterial cells.

In a preferred embodiment, the term "C4 body", as used herein, refers to any organic compound comprising a total of four carbon atoms, in any combination with functional groups comprising atoms other than carbon. In a more preferred embodiment, the term "C4 body", as used herein, refers to any derivate made from butanol or butyrate. In a most preferred embodiment, said derivative is obtained by a derivatization that involves any reaction other than those involving a net addition or removal" of carbon atoms to butanol or butyrate or derivatives thereof, including, but not limited to oxidation, in particular hydroxylation, reduction, and methyl shifts, wherein the feature "net addition or removal of carbon atoms" does not exclude a temporary addition or removal of carbon atoms, for example tethering the C4 body or derivative temporarily to an enzyme or a cofactor thereof. Examples of C4 bodies comprise 1-butanol (referred to in this application as "butanol"), 2-butanol, butyrate, 1,4-butanediol, 2,3-butanediol, amino butane, thiobutanol, isobutenol and isobutanol.

The present invention contemplates both the use of wild type acetogenic bacterial cells and genetically modified acetogenic bacterial cells. In a preferred embodiment, a genetically modified acetogenic bacterial cell is an acetogenic bacterial cell that has been modified such that the activity of at least one enzyme involved in the Wood-Ljungdahl pathway, i.e. the pathway converting carbon monoxide, carbon dioxide and hydrogen to acetate. In a preferred embodiment, the term "enzyme involved in the Wood-Ljungdahl pathway", as used herein, comprises any enzyme that binds to or, preferably accepts as a substrate, one of the substrates of said pathways, preferably carbon monoxide, carbon dioxide or hydrogen, or any of the intermediates formed within the pathway starting from any of these substrates as the substrates are converted to acetate or derivatives thereof. In another preferred embodiment, the term "enzyme involved in the Wood-Ljungdahl pathway", as used herein, refers to an enzyme from the group comprising CO dehydrogenase and acetyl-CoA synthetase (Diekert and Wohlfahrt, (1994) Antonie van Leeuwenhoek 66 (1-3), 209-221). Techniques that may be used to genetically modify bacterial cells are described in the prior art, for example in Sambrook et al. (Molecular Cloning—A Laboratory Manual (1989) Cold Spring Harbor Laboratory Press), as are methods for increasing the activity of an enzyme in a bacterial cell, for example by increasing expression of the gene encoding the enzyme having the activity of interest by way of chromosomal gene amplification (WO 03/014330 and WO 03/040373). In a preferred embodiment, the acetogenic bacterial cell is chosen from the group comprising *Clostridium carboxidivorans, Clostridium drakei* and *Clostridium ljungdahlii*.

It is essential that the process is carried out under anaerobic conditions. In a preferred embodiment, the term "anaerobic conditions", as used herein, means that the saturation of oxygen in a solution of interest is, in order of increasing preference, less than 30, 20, 10, 5, 2.5 or 1 percent saturation, wherein 100% saturation represents the concentration of oxygen present if the solution is sparged extensively with pure oxygen gas under comparable conditions, for example at 20° C. under atmospheric pressure. With regard to a gas, the term "anaerobic conditions", as used herein, means, in a preferred embodiment, that the gas comprises, in order of increased preference and with reference to the total volume, less than 30, 20, 10, 5, 2.5, 1, 0.5, 0.1, 0.01% oxygen. In another preferred embodiment, the term "anaerobic conditions", as used herein, means that the concentration of oxygen, either in a gas mixture or a solution, is such that it does not inhibit the growth of anaerobic acetogenic bacteria, preferably *Clostridium carboxidivorans*. The person skilled in the art is familiar with techniques that may be used to turn reaction vessels and solutions anaerobic, for example flushing gas tight vessel and solutions with nitrogen, argon or the like, or complementing aqueous solutions with enzymatic systems consuming oxygen, for example 0.6% (w/v) β-D-glucose, 0.5 units $ml^{-1}$ glucose oxidase (Sigma) and 200 units $ml^{-1}$ catalase (Sigma) as described by Richter, C. D. et al. (2002), J. Biol. Chem. 277 (5), 3094-3100.

Syngas is the main carbon source for the inventive production of C4 bodies, preferably butanol and/or butyric acid. In a preferred embodiment, the term "syngas", as used herein, refers to a mixture comprising at least one of water and hydrogen ($H_2$) and at least one of carbon monoxide (CO) and carbon dioxide ($CO_2$), wherein the total combined volume of water, hydrogen, carbon monoxide and carbon dioxide is at least 80, preferably 90 percent of the total volume of the mixture. Further components comprise nitrogen, noble gases and the like. In a preferred embodiment, the syngas comprises 40 to 95% carbon monoxide. In a preferred embodiment, the syngas comprises 40 to 100, preferably 40 to 95% carbon dioxide and 0.5 to 20% $H_2$. In another preferred embodiment, the syngas comprises less than 10% carbon dioxide. In another preferred embodiment, the syngas comprises less then 10% carbon monoxide. In another preferred embodiment the syngas comprises at least 5, preferably 10% carbon monoxide. In another preferred embodiment, the total combined volume of hydrogen and carbon dioxide is, in order of increasing preference, more than 50, 60, 70, 80, 90, 95 or 99 percent of the total volume of the mixture. In a preferred embodiment, the term "contacting" a microorganism with "syngas" of any composition specified in this application, as used herein means that the microorganism is present in an atmosphere consisting of syngas of the specified composition.

According to the inventive method, the acetogenic bacterial cell is contacted with syngas in the absence of oxygen in an aqueous medium. In a preferred embodiment, the term "aqueous medium" comprises any aqueous solution that comprises the amount of salts and buffers necessary to grow or sustain an acetogenic bacterial cell and to sustain acetogenesis. For example, an aqueous medium according to Hurst, K. M., and Lewis, R. (2010), Biochemical Engineering Journal 2010, 48, 159-165 may be used to carry out the inventive teachings. In a preferred embodiment, the aqueous medium comprises yeast extract.

A crucial aspect of the present invention is that ethanol ($CH_3$—$CH_2$—OH) and/or acetate ($CH_3$—$COO^-$) are present in the aqueous medium from the onset of the reaction at a total combined concentration, i.e. the sum of the concentration of the acetate cation and the concentration of ethanol, is at least 0.1 g $L^{-1}$. In other preferred embodiments, the concentration of ethanol and/or ethanol is 0.1 to 50, 0.2 to 40, 0.25 to 20 or 0.5 to 20 g $L^{-1}$.

Rather than waiting for the cell to produce endogenous acetate, exogenously produced acetate and/or ethanol is present initially in step a) in the aqueous medium. In a preferred embodiment, the term "exogenously produced" acetate and/or ethanol, as used herein, refers to acetate of ethanol produced or purified in a separate reaction vessel prior to contacting the acetogenic bacterial cell, by contrast to acetate and/or ethanol produced in step b), i.e. following step a). In a preferred embodiment, the term "exogenously produced" acetate and/or ethanol comprises acetate and/or ethanol produced by a acetogenic bacterial cell or in fact the same acetogenic bacterial cell as the one used in step a), but removed from the reaction vessel, separated from any C4 body produced and recycled. In a preferred embodiment, the concentration of exogenously produced acetate and/or ethanol is maintained in the aqueous medium at the value or range of values present initially as long as the reaction catalysed by the acetogenic bacterial cell in step b) continues. In a preferred embodiment, the acetate and/or ethanol in the aqueous medium as whole is regarded as exogenous as long as more than 80, preferably more than 90% of the total acetate and/or ethanol present in the aqueous medium is accounted for by exogenous produced acetate and/or ethanol.

The mixture obtained in step a) may be incubated for at least 0.5, 1, 2, 3, 5, 10, 12, 16, 24, 36, 48, 120 or 160 hours. In a preferred embodiment, a reducing agent is present in step b). The person skilled in the art is familiar with reducing agents, for example thiol-containing agents such as cysteine or dithionite. The initial concentration may be at least 0.1, 0.5, 1, 2, 5 or 10 mM.

It is preferred that the method comprises recycling ethanol and/or acetate from the mixture following step b). In a preferred embodiment, this means that some of the reaction mixture from step b) is removed and the acetate and/or ethanol therein is separated from any C4 body formed, followed by transferring the acetate and/or ethanol obtained in this manner back to the reaction mixture. Some of the reaction mixture may be removed in step b) in a batch-wise mode or, preferably, in a continuous mode. In the latter case, the reaction mixture removed continuously may be collected prior to the separation step.

The person skilled in the art is familiar with methods that may be used to separate acetate and/or ethanol from any butanol and/or butyric acid present in an aqueous solution, for example extraction using a hydrophobic organic solvent, distillation or the like.

Any organic compound referred to in this application, for example C4 bodies, acetate, ethanol, butyrate and butanol, comprises both protonated forms of the compound of interest as well as the various salts of the compound. For example, acetate may comprises both as acetic acid ($CH_3$—COOH), but also the various salts of acetic acid, for example sodium acetate ($CH_3$—$COO^-Na^+$), potassium acetate ($CH_3$—$COO^-K^+$), ammonium acetate ($CH_3$—$COO^-NH_4^+$) or the like.

In a preferred embodiment of the present invention, the invention is carried out in a continuous mode, wherein aqueous solutions from the vessel used to carry out steps a) and b) is continuously removed, separated into a fraction enriched in C4 bodies, preferably butanol and/or butyric acid, and another fraction enriched in acetate and/or ethanol, and the latter fraction is added to the vessel used to carry out steps a) and b).

The temperature in steps a) and b) needs to be chosen bearing in mind the needs of the acetogenic bacterial cell on the one hand and thermodynamic parameters on the other hand. The state of the art teaches ranges of temperatures as well as optimum temperatures for a vast range of acetogenic bacteria. For example, *Clostridium thermoaceticum* may be incubated at temperatures of up to 60° C. (Fontaine et al., 1942). See also standard textbooks of microbiology for temperatures that may be used to grow acetogenic bacterial and archaeal cells, for example Dworkin et al. (2006) The Prokaryotes—A Handbook on the Biology of Bacteria, Volume 2. In a preferred embodiment, the temperature applied in step b) is 0 to 100° C., 10 to 80° C., 20 to 60° C. and 30 to 45° C. The pressure of the syngas applied is, in a preferred embodiment, 0.5 to 10 bars, more preferably 0.8 to 8, even more preferably 1.5 to 6 bar. In another preferred embodiment, the pressure is more than 1, 1.5, 2, 3, 4, 5, 6, 7, 8, 9, 10 bar. In a preferred embodiment, the pressure applied exceeds atmospheric pressure. In a preferred embodiment, the unit "gauge pressure", as referred to herein, refers to the pressure relative to the local atmospheric or ambient pressure. For example, if the local atmospheric pressure is 1 bar and the pressure inside a vessel is 1.8 bar, then the gauge pressure is 0.8 bar (gauge pressure).

It is a particular strength of the present invention that the formation of C4 bodies, preferably butanol and/or butyric acid, does not depend on the presence of significant amounts of organic compounds comprising carbon chains of more than two carbon atoms. In a preferred embodiment, steps a) and b) may be, but do not have to be, carried out in the absence of carbohydrates. In a preferred embodiment, the term "in the absence of carbohydrates" means that the concentration of carbohydrates is, in order of increasing preference, less than 5, 1, 0.5, 0.1 or 0.05% (weight per volume). In a preferred embodiment, the term "carbohydrates" comprises any organic compound having at least two functional groups selected from the group comprising hydroxyl, aldehyde or keto groups and comprises a straight carbon chain of five or more carbon atoms. Exemplary carbohydrates comprise hexoses such as glucose or fructose, pentoses such as ribulose and complex sugars comprising two or more carbohydrate monomers, for example sucrose.

Likewise, it is preferred that the syngas, in order of increasing preference, provides more than 70, 75, 80, 85, 90 or 95% of the carbon present initially in step a). In a preferred embodiment, the term "syngas provides more than X % of the carbon present initially in step a)", as used herein, means that more than X % of the carbon atoms present in the reaction vessel are carbon atoms in carbon monoxide or carbon dioxide molecules. For example, syngas provides more than 90% of the carbon present if 9 moles of carbon dioxide, less than 1 mole methane and some hydrogen is present, but no other compounds comprising at least one carbon atom.

The process may be carried out in a batch-wise mode. If this is the case, the term "incubating the mixture . . . for at least X minutes" means, as used herein, in a preferred embodiment, that a batch of acetogenic bacterial cells in kept for X minutes under the conditions specified, for example in the presence of aqueous medium, the presence of syngas in contact with the acetogenic bacterial cell, the temperature set, the presence of ethanol and/or acetate and so on. Alternatively, the process may be carried out in a continuous mode. If this is the case, the term "incubating the mixture . . . for at least X minutes", means, as used herein, in a preferred embodiment, that the average time spent by a molecule of reactant, for example of hydrogen, in the vessel or the conditions specified is X minutes. For example, if a gas tight vessel comprises 10 liters of hydrogen, hydrogen is added at a flow rate of 1 liter per minute and the construction of the vessel is such that the hydrogen molecules may be assumed to leave the vessel in order of entrance, then the average time spent, in other words the time the hydrogen molecule spends incubated under the conditions set in the vessel, is 10 minutes.

If a large scale process is envisioned, it may be advantageous to carry out the inventive teachings in a continuous mode. In a preferred embodiment, the term "continuous mode", as used herein, refers to a method which comprises continuous substrate feed in the bioreactor and removal of medium comprising products from the bioreactor. The continuous mode may, in addition comprise a constant feed of nutrients. The cells in the bioreactor may grow, alternatively, nutrients may be limited to the effect that cells reach a stationary phase, i.e. growth is limited by the lack of nutrients, but cells remain metabolically active and keep converting substrates such as syngas. In a preferred embodiment, the term "stationary phase", as used herein, means that the cells undergoing such a phase are metabolically active by essentially do not multiply.

The invention may be carried out using any kind of vessel that allows for maintenance of anaerobic conditions. If carried out at a small scale, a gas tight glove providing a low-oxygen, or oxygen-free environment may be used. At a large scale, a high volume syngas fermenter appears more practical. In a preferred embodiment, the reaction mixture is subjected to constant stirring to ascertain that cells, nutrients, substrates and products are distributed uniformly throughout the aqueous medium.

State of the art analytical tools allow for the constant monitoring of numerous compounds in a bioreactor, for example by taking samples from the reaction mixture regularly and subjecting them to HPLC analysis. Key parameters such as pH and the concentration of substrates and products may be adjusted online if there is need. In a preferred embodiment, the concentration of at least one of ethanol and butanol under constant surveillance and the levels are adjusted to concentrations compatible with growth and catalytic activity of the acetogenic bacterial cell used.

The invention is further illustrated by the following figures and non-limiting examples from which further features, embodiments, aspects and advantages of the present invention may be taken.

BRIEF DESCRIPTIONS OF DRAWINGS

EXAMPLE 1: PRODUCTION OF BUTYRIC ACID IN THE ABSENCE OR PRESENCE OF ETHANOL

Figure 1:
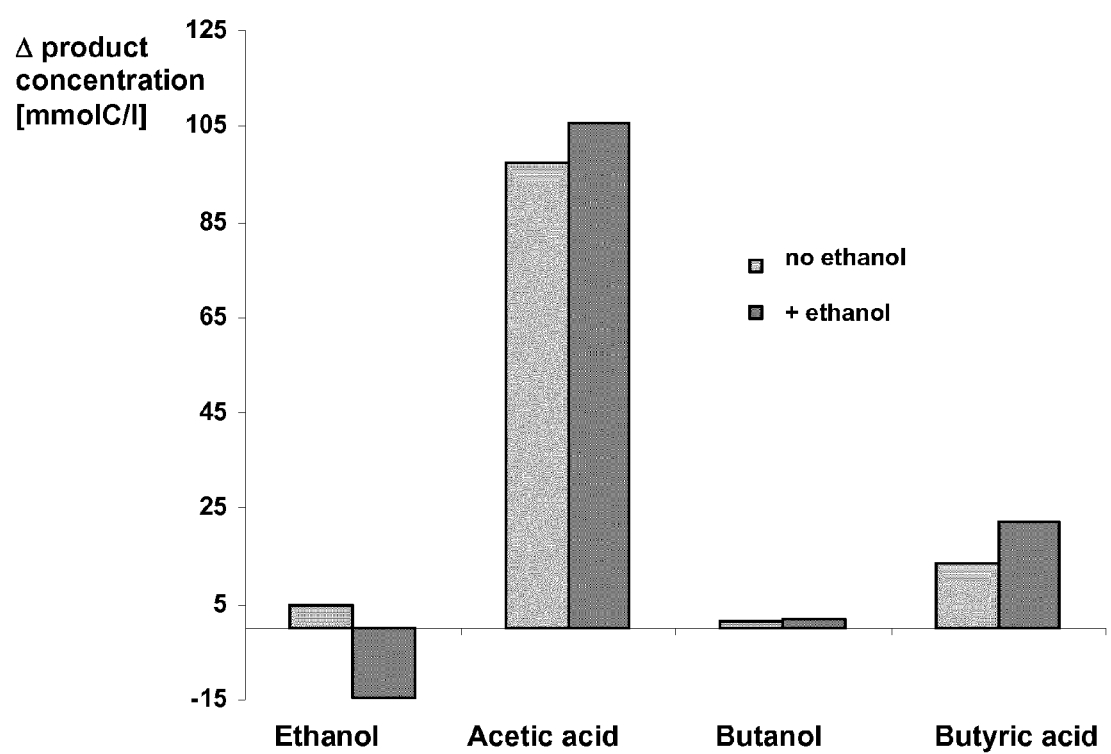
FIG. 1 shows the difference between product concentrations at the beginning and at the end of the cultivation with respect to the carbon content as obtained in Example 1. The unit "mmolC/l" refers to the amount of carbon in mmol per liter.

A *Clostridium carboxidivorans* DSMZ 15243 preculture was grown in anaerobic 1 L bottles sealed using a butylseptum, comprising 200 mL of modified PETC according to Hurst, K. M., and Lewis, R. (2010), Biochemical Engineering Journal 2010, 48, 159-165, consisting of 1 g yeast extract, 19 g MES, 30 mL mineral salt solution, 10 mL of trace element solution and 10 mL of vitamin solution. The mineral salt solution comprises 80 g NaCl, 100 g ammonium chloride, 10 g potassium chloride, 10 g potassium monophosphate, 20 g magnesium sulfate and 4 g calcium chloride per liter. The vitamin solution consists of 0.01 g pyridoxin, 0.005 g thiamin, 0.005 g riboflavin, 0.005 g calcium pantothenate, 0.005 g thioctacid, 0.005 g p-aminobenzoic acid, 0.005 g nicotinic acid, 0.005 vitamin B12, 0.002 g folic acid and 0.01 g MESNA per liter. The trace element solution consists of 2 g nitriloacetic acid, 1 g $MnSO_4$, 0.8 g iron ammonium sulfate, 0.2 g cobalt chloride, 0.2 g zinc sulfate, 0.02 g copper(II) chloride, 0.02 g nickel chloride, 0.02 g sodium molybdate, 0.02 g $Na_2SeO_4$, 0.02 $Na_2WO_4$ per liter. The pH was adjusted to 5.9.

Prior to inoculation the medium was boiled for 20 minutes and subsequently flushed with pure nitrogen for 20 minutes. Subsequently it was autoclaved at 121° C. for 20 minutes, followed by cooling down, then it was filled using process gas comprising 50% CO, 45% $H_2$ and 5% $CO_2$ at 1 bar gauge pressure. Subsequently, the pressure was adjusted to 0.8 bar gauge pressure.

Also, prior to inoculation, 1.5 mL of a solution comprising 4% each of sodium sulfate and cystein hydrochloride as reducing agent was added under sterile anaerobic conditions.

The culture was grown at 37° C. and 100 rpm. The culture was transferred to fresh medium every 72 hours.

For the experiments the medium was prepared in the same way using process gas comprising 95% CO and 5% $CO_2$. In addition, 0.6 g per liter ethanol was added to half the flasks under sterile anaerobic conditions.

The solutions were inoculated under sterile anaerobic conditions using 10 vol. % of inoculum from a 48 hour culture. The flasks were shaken at 37° C. at 100 rpm for 160 hours. The dry biomass and the product concentration were determined at the beginning and at the end of the experiment.

The concentrations of acetic acid, ethanol, butyric acid and butanol were determined using HPLC. A aminex HPX-87H column was used as a stationary phase. 5 mM sulfuric acid was used as an eluent at a constant flow rate of 0.6 mL/min. The temperature of the column was 40° C. Ethanol and butanol were detected using a refractive index detector. A diode array detector was used at a wave length of 210 nm to detect acetic acid and butyric acid. The concentrations of the compounds were calculated by integration of the peak using calibration graphs of the respective compound at defined concentrations.

FIG. 1 shows the difference between product concentrations at the beginning and at the end of the cultivation with respect to the carbon content.

In the presence of ethanol 105 nmolC/l acetic acid were formed compared to 97.17 mmolC/L formed in the absence of ethanol. 22.06 mmolC/L of butyric acid were formed in the presence of ethanol compared to 13.57 mmolC/L in the absence of ethanol, when equal amounts of dry biomass, more specifically 480 mg/L, were used.

In summary, addition of ethanol leads to a significant increase in the amount of butyric acid formed.

EXAMPLE 2: PRODUCTION OF BUTYRIC ACID IN THE ABSENCE OR PRESENCE OF ACETATE

The experimental protocol followed was as described in example 1, except for the fact that 2 g/L acetic acid was added to half the flask instead of 0.6 g/L ethanol and that the batch of syngas used comprised 50% carbon monoxide and 50% hydrogen.

Figure 2:
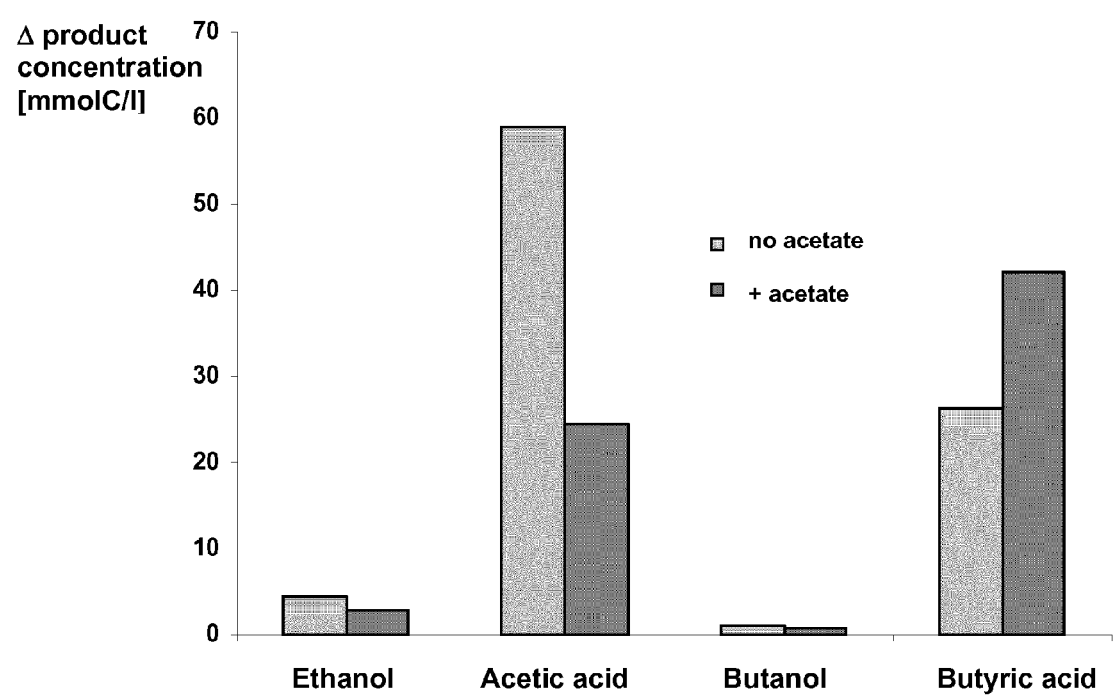
FIG. 2 shows the difference between product concentrations at the beginning and at the end of the cultivation with respect to the carbon content as obtained in Example 2. The unit "mmolC/l" refers to the amount of carbon in mmol per liter.

FIG. 2 shows the difference between product concentrations at the beginning and at the end of the cultivation with respect to the carbon content. In the presence of acetate 42.13 nmolC/l butyric acid was formed compared to 26.43 mmolC/L formed in the absence of acetate.

In summary addition of acetate also leads to an increase in the amount of butyric acid formed.

EXAMPLE 3: PRODUCTION OF BUTYRIC ACID IN THE PRESENCE OF ACETIC OR ETHANOL USING ALTERNATIVE STRAINS AND GAS MIXTURES

Media and Solutions Used:
ATCC 1754 modified (PETC minimal medium)

| Substance | Amount | |
|---|---|---|
| MES Solution | 10.00 | g/l |
| trace elements | 10 | ml/l |
| vitamins 141 | 10 | ml/l |
| fructose 250 g/L | 20 | ml/l |
| reducing agent ATCC | 10 | ml/l |

The substance was mixed with vitamins and trace elements and the volume adjusted pH value and NaOH solution using deminerialized water (VE water). Subsequently the pH value was adjusted to 6.0 using NaOH solution, the medium was boiled and transferred to pressure-resistant 1 l glass bottles. Subsequently, the medium was cooled on ice and sparged using $N_2$ in order to remove any remaining oxygen.

Subsequently, the medium was autoclaved. Then the reducing agent was added to the medium and the volume was adjusted using anaerobic VE water. The reducing agent was sterilized separately and stored under anaerobic conditions.

ATCC 1754 modified (PETC)

| Substance | Amount | |
|---|---|---|
| $NH_4Cl$ | 1.00 | g/l |
| KCl | 0.10 | g/l |
| $MgSO_4 \times 7H_2O$ | 0.20 | g/l |
| NaCl | 0.80 | g/l |
| $KH_2PO_4$ | 0.10 | g/l |
| $CaCl_2 \times 2H_2O$ | 20.00 | mg/l |
| resazurine | 1.00 | mg/l |
| yeast extract | 1.00 | g/l |
| MES Solution | 20.00 | g/l |
| trace elements ATCC 1754 | 10 | ml/l |
| vitamins 141 | 10 | ml/l |
| fructose 250 g/L | 20 | ml/l |
| reducing agent ATCC | 10 | ml/l |

The substance, vitamins and trace elements were mixed and the volume adjusted pH value and NaOH solution using deminerialized water (VE water). Subsequently, the pH value was adjusted to 6.0 using NaOH solution, the medium was boiled and transferred to pressure-resistant 1 l glass bottles. Subsequently the medium was cooled on ice and sparged using $N_2$ in order to remove any remaining oxygen.

Subsequently, the medium was autoclaved. Then the reducing agent was added to the medium and the volume was adjusted using anaerobic VE water. The reducing agent was sterilized separately and stored under anaerobic conditions.

ATCC 1754 modified (PETC modified)

| Substance | Amount | |
|---|---|---|
| yeast extract | 1.00 | g/l |
| MES | 10.00 | g/l |
| Solution | | |
| trace elements ATCC 1754 | 10 | ml/l |
| vitamins PETC mod | 10 | ml/l |
| mineral solution PETC mod | 30 | ml/l |
| reducing agent ATCC | 7.5 | ml/l |

The substance, vitamins and trace elements were mixed and the volume adjusted pH value and NaOH solution using deminerialized water (VE water). Subsequently, the pH value was adjusted to 6.0 using NaOH solution, the medium was boiled and transferred to pressure-resistant 1 l glass bottles. Subsequently the medium was cooled on ice and sparged using $N_2$ in order to remove any remaining oxygen.

Subsequently, the medium was autoclaved. Then the reducing agent was added to the medium and the volume was adjusted using anaerobic VE water. The reducing agent was sterilized separately and stored under anaerobic conditions.

trace elements ATCC 1754

| Substance | Amount | |
|---|---|---|
| nitrilotriacetic acid | 2 | g/l |
| $MnSO_4 \times H_2O$ | 1 | g/l |
| $(NH_4)_2Fe(SO_4)_2 \times 6H_2O$ | 0.8 | g/l |
| $CoCl_2 \times 6H_2O$ | 0.2 | g/l |
| $ZnSO_4 \times 7H_2O$ | 0.2 | g/l |
| $CuCl_2 \times 2H_2O$ | 0.02 | g/l |
| $Na_2MoO_4 \times 2H_2O$ | 0.02 | g/l |
| $NiCl_2 \times 6H_2O$ | 0.02 | g/l |
| $Na_2SeO_4$ | 0.02 | g/l |
| $Na_2WO_4 \times 2H_2O$ | 0.02 | g/l |

First of all, the nitrilotriacetic acid was dissolved in 1 l demineralized water (VE water), and the pH value was adjusted to 6.0 using a KOH solution. Subsequently, all the other chemicals were added. The trace element solution was stored at 4° C. in the dark.

Vitamins 141

| Substance | Amount | |
|---|---|---|
| biotin | 2 | mg/l |
| folic acid | 2 | mg/l |
| pyridoxine-HCl | 10 | mg/l |
| thiamine-HCl × $H_2O$ | 5 | mg/l |
| riboflavine | 5 | mg/l |
| nicotinic acid | 5 | mg/l |
| D-Ca-pantothenate | 5 | mg/l |
| vitamin B12 | 0.1 | mg/l |
| p-amino benzoic acid | 5 | mg/l |
| liponic acid | 5 | mg/l |

The substances were solved in 1 l demineralized water (VE water) and frozen at −20° C. in sterile falcon tubes in 10 ml portions until use.

Mineral Solution PETC Mod

| Substance | Amount | |
|---|---|---|
| NaCl | 80 | g/l |
| $NH_4Cl$ | 100 | g/l |
| KCl | 10 | g/l |
| $KH_2PO_4$ | 10 | g/l |
| $MgSO_4 \times 7H_2O$ | 20 | g/l |
| $CaCl_2 \times 2H_2O$ | 4 | g/l |

The substances were dissolved in 1 l demineralized water (VE water). The mineral solution was stored at 4° C. in the dark.

Reducing agent ATCC 1754

| Substance | Amount | |
|---|---|---|
| NaOH | 9 | g/l |
| L-Cysteine × HCl | 40 | g/l |
| $Na_2S \times 9H_2O$ | 40 | g/l |

First of all NaOH was dissolved in 1 l demineralized water (VE water) and boiled. Subsequently the solution was transferred to a pressure-resistant 1 l glass bottle and spaged using $N_2$ while cooling down on ice. The other substances were added while the solution cooled down. Subsequently, the reducing agent was autoclaved for 20 minutes.

Strains Used:
COX-Cdr-001 (*Clostridium drakei*)
COX-Clj-001 (*Clostridium ljungdahlii*)

Pre-Cultures:

The strains used were transferred to pre-cultures using working cryocultures prepared immediately (prior to cultures using 4 ml culture in the exponential phase and 1 ml 50% glycerol solution for conservation, storage at −80° C.). The pre-cultures each consisted of 5 ml ATCC 1754 mod (PETC)-medium and a fixed inoculum of the strains. The ideal inoculum density was determined in pilot experiments for the respective strain.

COX-Cdr-001: 0.1% in 5 ml medium
COX-Clj-001: 10% in 5 ml medium

Cultures:

50 ml each of any medium used was transferred into sterile anaerobic (oxygen-free) pressure-resistant 250 ml glass bottles and inoculated using 10% (5 ml) of the strains used taken from the freshly prepared 3 days old pre-cultures.

The culture flasks were closed using a sterile butyl bung and a red lid (comprising three drilled wholes). Hollow needles (company Sterican, Ø0.90×40 mm) were pierced through all three wholes. A manometer for controlling pressure was attached to one of the hollow needles (ideally the one in the middle). Valves were attached to the other hollow needles, so gas added and gas removed from the culture flask could be controlled independent from each other.

Each of the strains used were cultivated in duplicate for direct reproducible results.

Preparation of Cultures:

Prior to starting the actual cultivations the bottles were each sparged using syngas thrice. This was done by attaching to one of the valves a tube for pumping gas into the bottle and to the other valve a tube for releasing the gas removed under the hood in line with regulations.

By opening the valve with the tube for adding gas syngas was pumped into the culture flask until the needle of the manometer displayed a pressure value of 0.8 bar. Subsequently the valve for adding gas was closed and the valve for removing gas was opened until the needle displayed a pressure value of 0 bar. This procedure was repeated thrice for each culture flask. When the procedure was repeated for the fourth time the pressure in the bottle was maintained, i. e. the cultures were over laid with syngas.

The culture samples were then ready for cultivation at 35° C. and 100 rpm in a rocking water bath.

Taking Samples:

One or twice per day approximately 1 ml of culture was removed for determining the optical density at 600 nm (recording the growth of a culture).

Initially and at the end of the experiments two samples of 1.5 ml each were transferred to 2 ml Eppendorf-tubes and used for NMR-analysis.

Addition of Gas:

In regular intervals (several times a day) the pressure inside the culture flask was checked in order to ensure that it was constant. The growth of the cultures and their metabolism consumed varying amounts of syngas. In case the pressure decreased further gas was added as described above. The same procedure was carried out if gas was removed from the culture flask before taking a sample.

End of the Experiment:

The experiment was terminated after approximately one week by sparging continuously for 10 minutes nitrogen through every culture flask before removing the hollow needles for increased safety. The cultures were transferred to sterile 50 ml falcon tubes under a sterile hood and spun down for 30 minutes at 4500 g. There was no need to work under anaerobic conditions any more. The cell pellets recovered were discarded and the supernatants of the cultures were transferred to sterile 50 ml syringes under the sterile hood. They were transferred to a new sterile 50 ml falcon tube via a 0.2 µm sterile filter and frozen at −20° C. as back up samples.

Experiment 1: Cultivation Using Yeast Extract and 0.6 g/l Ethanol (BF-DM-12-COX-038)

The experiments were carried out using modified ATCC 1754 (PETC)-medium comprising 1 g/l yeast extract. In addition 0.6 g/l ethanol were used as a carbon source. The gas mixture used comprised 30% $CO_2$ and 70% $H_2$.

Experiment 2: Cultivation Using Yeast Extract and 2 g/l Acetic Acid (BF-DM-12-COX-041)

The experiment was carried out as described in experiment 1 except that acetic acid was added to the medium rather than ethanol.

Experiment 3: Cultivation Using Yeast Extract (BF-DM-12-COX-042) (Comparative Experiment)

For direct comparison the same medium was used but without addition of ethanol or acetic acid.

Figure 3:
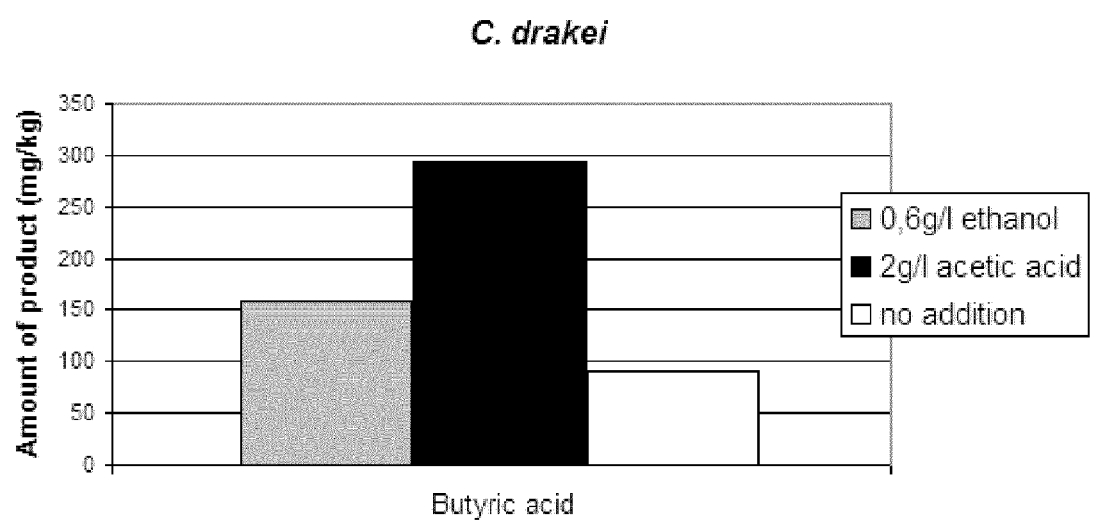
FIG. 3 shows the amounts of product at the beginning and at the end of the cultivation with respect to the carbon content as obtained in Example 3 using strain *Clostridium drakei*.
Figure 4:
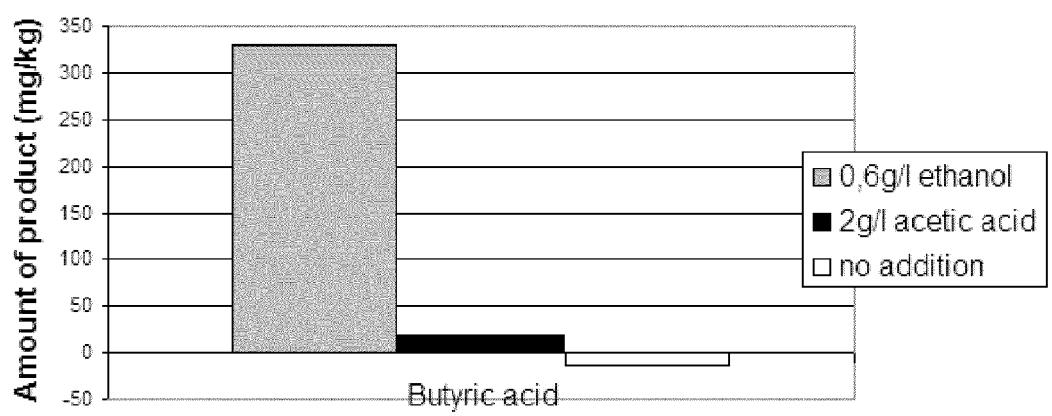
FIG. 4 shows the difference between product concentrations at the beginning and at the end of the cultivation with respect to the carbon content as obtained in Example 3 using strain *Clostridium ljungdahlii*.

The results are depicted in FIGS. 3 and 4. In summary, the effect shown in Example 1 could be reproduced using alternative gas mixtures and other strains of acetogenic bacteria.

The invention claimed is:

1. A method for producing a C4 compound, the method comprising:
    contacting an acetogenic bacterial cell in an aqueous medium with syngas under anaerobic conditions in the absence of carbohydrates, wherein the aqueous medium comprises ethanol, an acetate, or both, in a total concentration of at least $0.1 \text{ g L}^{-1}$, wherein at least a portion of the ethanol, acetate, or both, is present in the aqueous medium before the acetogenic bacterial cell is brought into contact with the aqueous medium, thereby obtaining a mixture; and
    incubating the mixture at a temperature between 0 and 100° C. for at least 30 minutes, to obtain a C4 compound.

2. The method according to claim 1, wherein the total concentration of the ethanol and the acetate is from 0.5 to 20 $\text{g L}^{-1}$.

3. The method according to claim 1, wherein the syngas comprises from 40 to 100% of CO.

4. The method according to claim 1, wherein the syngas comprises less than 10% of $CO_2$.

5. The method according to claim 1, wherein the syngas comprises less than 10% of CO.

6. The method according to claim 1, further comprising:
    separating and, optionally, recycling to the aqueous medium, the ethanol, the acetate, or both, from the mixture following said incubating.

7. The method according to claim 1, wherein the acetogenic bacterial cell is selected from the group consisting of *Clostridium*, *Moorella* and *Carboxythermus*.

8. The method according to claim 1, wherein a pH in said contacting and incubating is maintained between 3 and 7.

9. The method according to claim 1, wherein said incubating is carried out at a temperature between 15° C. and 45° C.

10. The method according to claim 1, wherein the syngas provides more than 80% of carbon present initially in said contacting.

11. The method according to claim 1, wherein the method is run in a continuous mode.

12. The method according to claim 1, wherein said incubating is carried out in the absence of carbohydrates.

13. A method for increasing a proportion of syngas converted by an acetogenic bacterial cell in an aqueous medium, the method comprising:
    introducing ethanol, an acetate, or both, into an aqueous medium comprising an acetogenic bacterial cell, where syngas is converted by the acetogenic bacterial cell under anaerobic conditions in the absence of carbohydrates to a C4 compound,
    wherein the ethanol, the acetate, or both, are exogenously added to the aqueous medium prior to accumulation of detectable quantities of ethanol and acetate produced endogenously by the cell.

14. The method according to claim 13, wherein the acetate and ethanol are present in the aqueous medium comprising the acetogenic bacterial cell at a total concentration of 0.5 to 5 $\text{g L}^{-1}$.

15. The method according to claim 13, wherein the acetogenic bacterial cell is selected from the group consisting of *Clostridium*, *Moorella* and *Carboxythermus*.

16. The method according to claim 1, wherein the C4 compound is butyric acid.

17. The method according to claim 1, wherein the C4 compound is butanol.

18. The method according to claim 1, wherein the syngas comprises from 40 to 95% of CO.

19. The method according to claim 1, wherein the aqueous medium comprises ethanol.

20. The method according to claim 1, wherein the aqueous medium comprises the acetate.

* * * * *